(12) United States Patent
Wang et al.

(10) Patent No.: US 6,646,064 B2
(45) Date of Patent: Nov. 11, 2003

(54) REACTING EPOXY RESIN WITH P-CONTAINING DIHYDRIC PHENOL OR NAPHTHOL

(75) Inventors: Chun-Shan Wang, Tainan (TW); Jeng-Yueh Shieh, Tainan (TW)

(73) Assignee: National Science Council, Taipei (TW)

( * ) Notice: Subject to any disclaimer, the term of this patent is extended or adjusted under 35 U.S.C. 154(b) by 110 days.

(21) Appl. No.: 09/950,468

(22) Filed: Sep. 10, 2001

(65) Prior Publication Data

US 2002/0035233 A1 Mar. 21, 2002

Related U.S. Application Data

(63) Continuation of application No. 09/261,884, filed on Mar. 3, 1999, now Pat. No. 6,291,626.

(30) Foreign Application Priority Data

Jun. 19, 1998 (TW) ........................................ 87109911 A

(51) Int. Cl.$^7$ ........................ C08G 59/06; C08G 59/08; C08G 59/14
(52) U.S. Cl. ........................ 525/523; 525/480; 525/481; 525/533; 528/99; 528/112; 528/119; 528/121; 528/124
(58) Field of Search ................................ 525/480, 481, 525/523, 533; 528/99, 112, 119, 121, 124

(56) References Cited

FOREIGN PATENT DOCUMENTS

EP 806429 A2 * 11/1997

OTHER PUBLICATIONS

Strutkol Polydis brochure, "Reactive, halogen–free flame retardants for epoxies," Schill + Seilacher, Sep. 1997, p. 6.*
Addcon World '98 lecture, "Reactive, Halogen–Free Flame Retardants For Epoxies" by Sprenger et al., The International Plasti Additives and Modifiers Conference, Nov. 1998, Rapra Technology, Ltd. pp. 1–5.*
Sprenger et al., "New developments in flame retarded adhesives," kleben & dichten Adhasion, Schill + Seilacher, Sep. 1998, four pages.*
Chun–Shan Wang and Jeng–Yueh Shieh, "Synthesis and Properties of Epoxy Resins Containing 2-(6-oxid-gH-dibenz{c,e}{1,2} oxaphosphorin-6-yl) 1,4-benzenediol," Polymer, vol. 39. No. 23, 1998, pp. 5819–5826.

* cited by examiner

Primary Examiner—Robert E. L. Sellers
(74) Attorney, Agent, or Firm—Jackson Walker L.L.P.

(57) ABSTRACT

A method for imparting flame retardance to an epoxy resin comprises reacting an epoxy resin with a phosphorus-containing dihydric phenol or naphthol derived from the reaction of 9,10-dihydro-9-oxa-10-phosphaphenanthrene-10-oxide (i.e., DOPO) with a benzoquinone or naphthoquinone.

5 Claims, No Drawings

REACTING EPOXY RESIN WITH P-CONTAINING DIHYDRIC PHENOL OR NAPHTHOL

RELATED APPLICATION

This application is a continuation of patent application Ser. No. 09/261,884, filed Mar. 3, 1999, now U.S. Pat. No. 6,291,626.

FIELD OF THE INVENTION

The present invention relates generally to flame-retardant advanced epoxy resins prepared from a bisphenol having phosphorus group. The present invention also relates to cured epoxy resins resulting from the advanced epoxy resins, which have excellent flame-retardancy and mechanical properties

BACKGROUND OF THE INVENTION

Epoxy resins have the excellent characteristics of moisture, solvent and chemical resistance, toughness, low shrinkage on cure, superior electrical and mechanical resistance properties, and good adhesion to many substrates. The versatility in formulation also make epoxy resins widely applicable industrially for surface coatings, adhesive, painting materials, potting, composites, laminates, encapsulants for semiconductors, and insulating materials for electric devices, etc. O-Cresol formaldehyde novolac epoxy (CNE) is the resin typically employed in the encapsulation of microelectronic devices. Several approaches for modification of epoxy backbone for enhancing the thermal properties of epoxy resins have been reported. Aromatic bromine compounds in conjunction with antimony oxide are widely used as a flame-retardant for epoxy resins. Tetrabromobisphenol A is a typical example of the aromatic bromine compounds used as a flame-retardant for epoxy resins. An excess amount of epoxy resin is reacted with tetrabromobisphenol A to prepare an advanced epoxy resin having two terminal epoxide groups, as shown in the following formula:

employed to encapsulate microelectronic devices, in which the advanced epoxy resin is cured at a high temperature with a curing agent, so that an encapsulant having a flame-retardant property is formed. Typical examples can be found in U.S. Pat. No. 3,040,495 (1961); U.S. Pat. No. 3,058,946 (1962); U.S. Pat. No. 3,294,742 (1966); U.S. Pat. No. 3,929,908 (1975); U.S. Pat. No. 3,956,403 (1976); U.S. Pat. No. 3,974,235 (1976); U.S. Pat. No. 3,989,531 (1976); U.S. Pat. No. 4,058,507 (1997); U.S. Pat. No. 4,104,257 (1978); U.S. Pat. No. 4,170,711 (1979); and U.S. Pat. No. 4,647,648(1987).

Although the tetrabromobisphenol A-containing advanced epoxy resin shows flame-retardant property, major problems encountered with this system are concerned with the generation of toxic and corrosive fumes during combustion such as dioxin and benzofuran.

The flame-retardant having a small molecular weight tends to degrade the mechanical properties of the epoxy resins, and migrate/vaporize from the epoxy resins such that the flame retardancy thereof diminishes.

The trend of electronics equipment is being miniaturized and becoming thinner, at the same time the scale of integration of large scale integrated circuits (LSICs) is continuing upward, forcing the design toward larger chips, finer patterns, and higher pin counts that are more susceptible to a high-temperature failure. The prevailing surface mount technology (SMT) also causes the devices to be subjected to a high temperature. Therefore, the development of a high-temperature reliable, flame-retardant and environmentally friendly epoxy resin for printed circuit board and encapsulant are essential for semiconductor industry.

It is an object of this invention to provide flame-retardant advanced epoxy resins and cured epoxy resins with good thermal stability, superior heat resistance, and environment friendly, which are suitable for use in making printed circuit boards and in semiconductor encapsulation applications.

It is another object of this invention to provide a method for improving flame-retardant properties of epoxy resins.

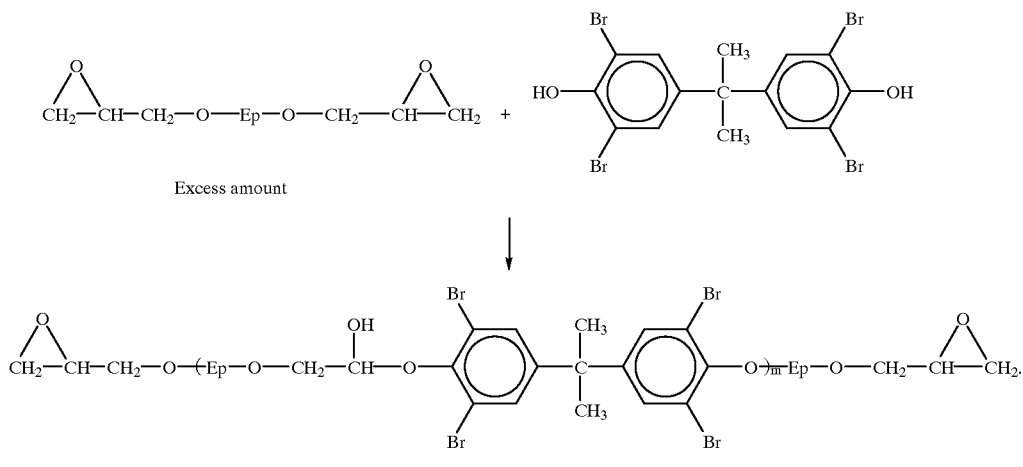

A flame-retardant advanced epoxy resin, wherein EP is a bi-radical group of the backbone of the epoxy resin, and m is an integer of 1–10. The advanced epoxy resin can be used in preparing a flame-retardant printed circuit board (FR-4) by impregnating glass fibers with the advanced epoxy resin and heating the resulting composite to cure the advanced epoxy resin. Furthermore, the advanced epoxy resin can be

SUMMARY OF THE INVENTION

In order to accomplish the aforesaid objects, a flame-retardant advanced epoxy resin and a cured epoxy resin disclosed in the present invention have the following formula (I):

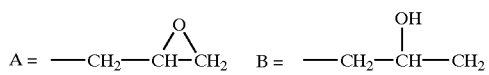 (I)

wherein:
m is greater than 0 and less than 10;
X=A or B, wherein:

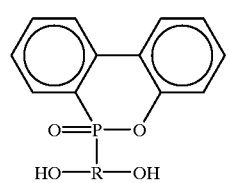

when X=A, the formula (I) represents the advanced epoxy resin, X=B, the formula (I) represent the cured epoxy resin;

wherein $R_1$ is hydrogen or $C_{1-4}$ hydrocarbon group; wherein

, wherein

or a phenol-aldehyde novolac epoxy resin backbone, and when Ep is the phenol-aldehyde novolac epoxy resin backbone, the flame-retardant advanced epoxy resin and the cured epoxy resin represented by the formula (I) is prepared by reacting a dihydric phenol or naphthol having the following formula (III):

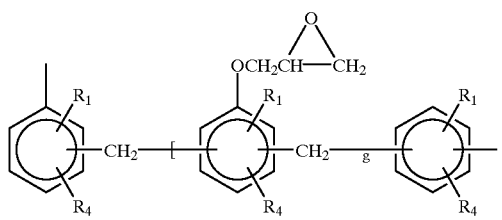 (III)

wherein R is the same as defined above, with a phenol-aldehyde novolac epoxy resin having the following formula (II'):

 (II')

wherein $R_1$ is the same as defined above, g is an integer of 1–6, and $R_4$ and $R_5$ independently are hydrogen or —$CH_3$.

The flame-retardant advanced epoxy resin and cured epoxy resin of the present invention contain a rigid phosphorus group, which provide not only the better flame-retardant effect and thermal stability than those prepared with a conventional aromatic bromine group, but also generate much less fumes in the combustion test.

DETAILED DESCRIPTION OF THE INVENTION

The present invention provides an advanced epoxy resin and a cured epoxy resin containing a flame-retardant phosphorus group, which may be represented by the following formula (I), (I)

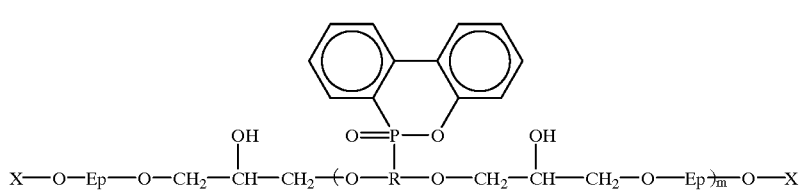

wherein m, X, $E_p$ and R are defined as above.

A suitable method for preparing the flame-retardant advanced epoxy resin and cured epoxy resin represented by the formula (I) comprises reacting an epoxy resin having the following formula (II) and a phosphorus-containing dihydric phenol or naphathol having the following formula (III) in a molten state or in a common solvent and in the presence of a catalyst:

(II)

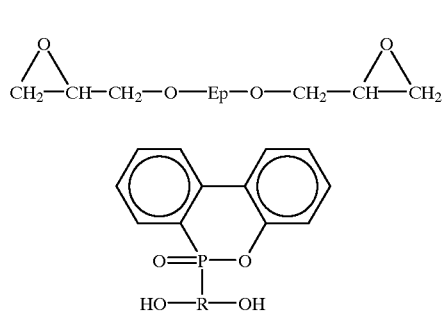

(III)

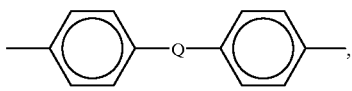

wherein Ep and R are the same as defined above.

Preferably, Ep in the formula (I) is

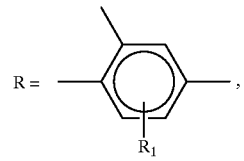

wherein Q is —C(CH$_3$)$_2$—, or $E_p$ is a phenol-aldehyde novolac epoxy resin backbone having the following formula:

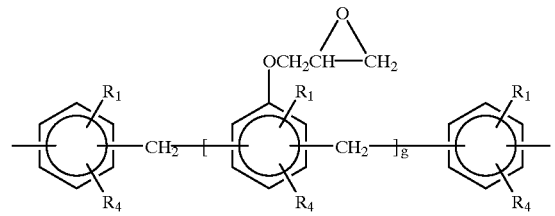

wherein $R_1$ is hydrogen and $R_4$ is —CH$_3$.

Preferably, R in the formula (I) is

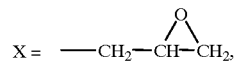

wherein $R_1$ is defined as above.

In the method for preparing the flame-retardant advanced epoxy resin and cured epoxy resin compound (I), the advanced epoxy resin (I'), i.e. X in the formula (I) is $$X = \text{—CH}_2\text{—CH—CH}_2,$$

is prepared when an excess amount of epoxy resin (II) is used to react with phosphorus-containing dihydric phenol or naphthol (III) as shown in the following reaction:

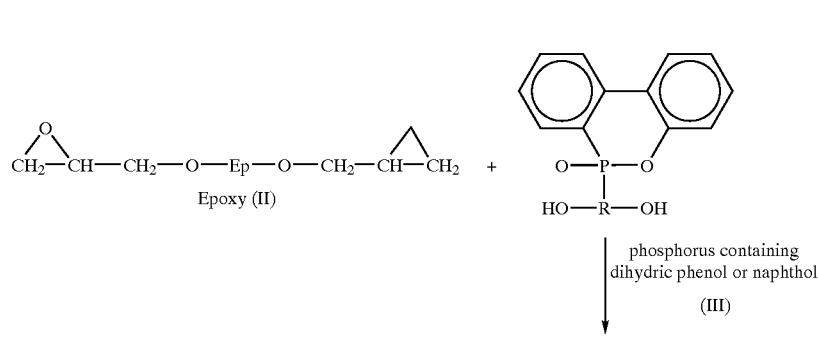

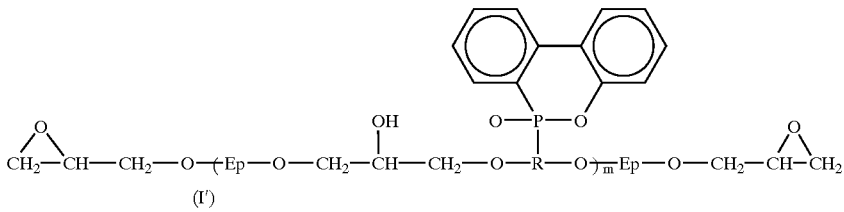

(I')

wherein R, Ep, and m are the same as defined above. Preferably, this reaction is carried out at 100° C.–200° C., more preferably at 150° C.–180° C., and in the presence of a catalyst selected from the group consisting of 2-phenylimidazole, 2-methylimidazole, triphenylphosphine, a quarternary phosphoium compound and a quarternary ammonium compound. Examples of the quarternary phosphoium compound include ethyltriphenyl phosphonium acetate and ethyltriphenyl phosphonium halides. Examples of the quarternary ammonium compound are benzyltrimethyl ammonium chloride, benzyltriethyl ammonium chloride and tetrabutyl ammonium chloride. Preferably, the equivalent ratio of the epoxy resin (II) to the hydroxyl group in the bisphenol compound (III) ranges from 1.5:1 to 5:1; and more preferably 2:1 to 3:1.

In the method for preparing the flame-retardant cured epoxy resin, i.e. X in the formula (I) is B, the phosphorus-containing dihydric phenol or naphthol (III) was used as a curing agent of the epoxy resin (II). The dihydric phenol or naphthol (III) can be used alone or together with another curing agent such as phenol-formaldehyde novolac, dicyandiamide, methylenedianiline, diaminodiphenyl sulfone, phthalic anhydride and hexahydrophthalic anhydride. A suitable amount of the curing agent for curing the epoxy resin (II) is the equivalent ratio of the epoxide group in the epoxy resin (II) and the functional groups in the curing agent ranging from 1:1 to 1.2:1.

It is apparent that the present invention also provides a method for improving flame-retardant properties of the epoxy resin (II), which comprises reacting said epoxy resin with the phosphorus-containing dihydric phenol or naphthol (III), in which the epoxide group of said epoxy resin is reacted with the hydroxyl group of said phosphorus-containing containing dihydric phenol or naphthol so that an open ring reaction of said epoxide group occurs.

A suitable epoxy resin for use in the present invention can be any known epoxy resin, for examples those having two epoxide groups such as bisphenol A epoxy resin, bisphenol F epoxy resin, bisphenol S epoxy resin and bisphenol epoxy resin, and those having more than two epoxide groups such as phenol formaldehyde novolac epoxy and cresol formaldehyde novolac epoxy (CNE).

The phosphorous-containing containing dihydric phenol or naphthol (III) used in the present invention can be synthesized according to the following reaction (IV):

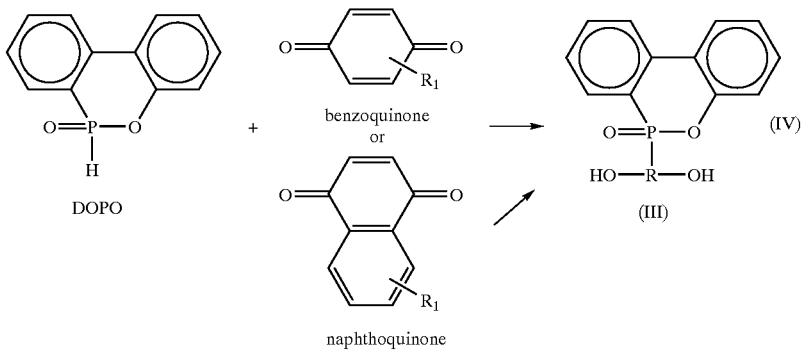

wherein $R_1$ and R are the same as defined above. The reaction (IV) is preferably carried out at a temperature range of 80° C.–120° C. in an appropriate solvent such as toluene.

EXAMPLES

I. The Preparation of a Phosphorus-Containing Dihydric Phenol or Naphthol

Preparation Example 1: (DOPO-BQ)

500 g of 2-(2-hydroxyphenyl)phenylphosphonic acid (HPPA) was placed in a 300 ml flask which was connected to a vacuum system. The content was heated to its molten state (106° C.) under full vacuum for dehydration. The temperature was slowly increased from 106 to 160° C. until the dehydration was complete. White solids of DOPO (9,10-dihydro-9-oxa-10-phosphaphenanthrene-10-oxide) (yield 93%) with m.p. 119–1200 C. after recrystallization from tetrahydrofuran was obtained. I.r.: 1168, 965 (P-Ph), 1196 (P=O), 2384 (P—H), 1587 cm$^{-1}$ (P-Ph). Anal. Calcd. for $C_{12}H_9O_2P$: C, 66.67; H, 4.17; O, 14.81; P, 14.35. Found: C, 66.64; H, 4.31; O, 14.59; P, 14.66. MS, m/z: 216 (100, M$^+$).

To a one liter four-inlet flask equipped with a temperature controller, a reflux condenser, a nitrogen feed and a mechanical stirrer, 1 mole DOPO (9,10-dihydro-9-oxa-10-phosphaphenanthrene-10-oxide, 216 g) and 500 ml toluene were added. The mixture was heated to 70° C. and then stirred. The mixture was heated to a temperature of 90° C. and the stirring was continued until DOPO was dissolved completely. To this solution was added slowly 0.9 mole (97 g) 1,4-benzoquinone (BQ), and the temperature thereof was increased to 110° C. and maintained at that temperature for two hours after the addition of BQ was completed. The mixture was then cooled to room temperature, filtered, and dried to obtain 2-(6-oxido-6H-dibenz<c,e><1,2>oxaphosphorin 6-yl)-1,4-benzenediol (DOPO-BQ). Yield, 98%; m.p. 258–259° C.

Preparation Example 2: (DOPO-MBQ)

A bisphenol DOPO-MBQ was prepared from 1 mole DOPO and 0.9 mole methyl-1,4-benzoquinone (MBQ) according to the same procedures as described in Preparation example 1. Yield, 97%; m.p. 263–265° C.

Preparation Example 3: (DOPO-NQ)

A bisphenol DOPO-NQ was prepared from 1 mole DOPO and 0.9 mole 1,4-naphthoquinone (NQ) according to the same procedures as described in Preparation example 1. Yield, 85%; m.p. 282–283° C.

Preparation Example 4: (DOPO-MNQ)

A bisphenol DOPO-MNQ was prepared from 1 mole DOPO and 0.9 mole 2-methyl-1,4-naphthoquinone (MNQ) according to the same procedures as described in Preparation example 1. Yield, 83%; m.p. 289–291° C.

II. The Preparation of an Advanced Epoxy Resin Containing Phosphorus Group

Example 1

An advanced epoxy resin prepared from bisphenol A epoxy resin and DOPO-BQ

To a one liter reactor equipped with a temperature controller, a reflux condenser, a nitrogen feed, a vacuum system and a mechanical stirrer, 400 g diglycidyl ether of bisphenol A (BPA epoxy resin) having an epoxide equivalent weight (EEW) of 185 was added, and heated to 110° C. while stirring and vacuuming (<100 mmHg) for a period of 30 minutes to remove a trace amount of water contained in the epoxy resin. The vacuuming was stopped, and dried nitrogen was introduced into the reactor until the atmospheric pressure was reached. The temperature of the reactor was raised to 130° C., and 210 g DOPO-BQ was then added while stirring. After a molten mixture of DOPO-BQ and BPA epoxy resin was formed, 500 ppm (based on total weight) ethyl triphenyl phosphonium chloride was added, and the temperature of the reaction mixture was increased to 160° C. and maintained at 160° C. for two hours. The equivalent ratio of epoxide group to hydroxyl group was 2.20/1. The resultant product had an EEW of 483

Example 2

The procedures described in Example 1 were repeated, except that DOPO-BQ (Preparation example 1) was replaced with DOPO-MBQ (Preparation example 2). The resultant product had an EEW of 483.

Example 3

The procedures described in Example 1 were repeated, except that DOPO-BQ (Preparation example 1) was replaced with DOPO-NQ (Preparation example 3). The resultant product had an EEW of 483.

Example 4

The procedures described in Example 1 were repeated, except that DOPO-BQ (Preparation example 1) was replaced with DOPO-MNQ (Preparation example 4). The resultant product had an EEW of 483.

Control Example 1:

The procedures described in Example 1 were repeated, except that DOPO-BQ (Preparation example 1) was replaced with bisphenol A and the equivalent ratio of epoxide group to hydroxyl group was 2.04:1 instead of 2.20:1. The resultant product had an EEW of 483.

Control Example 2:

The procedures described in Example 1 were repeated, except that DOPO-BQ (Preparation example 1) was replaced with tetrabromobisphenol A and the equivalent ratio of epoxide group to hydroxyl group was 2.58:1 instead of 2.20:1. The resultant product had an EEW of 483.

III. The preparation of a cured epoxy resin from an advanced epoxy resin

Example 5

Cured epoxy resins were prepared from the advanced epoxy resins prepared in Examples 1–4 and Control Examples 1–2 with a curing agent (methylene dianiline).

Various advanced epoxy resins were mixed with methylene dianiline (1:1 equivalent ratio) at 150° C. and poured into a hot aluminum mould, cured in an oven at 175° C. for one hour, and then postcured at 200° C. for two hours.

The flexural properties of the resulting cured epoxy resins were shown in Table 2. The thermogravimetric analysis data of the resulting cured epoxy resins were shown in Table 3. The flame-retardant properties of the resulting cured epoxy resins were shown in Table 4.

TABLE 1

The flexural strength

| Specimens | Flexural strength at 50° C., dyne/cm$^2$ |
| --- | --- |
| Control Ex. 1 | 5.4 |
| Control Ex. 2 | 5.6 |
| Example 1 | 6.8 |
| Example 2 | 6.9 |
| Example 3 | 6.9 |
| Example 4 | 6.9 |

TABLE 2

The thermogravimetric analysis data

| Specimens | Temperature of 5 wt % loss (° C.) | Maximum thermal degradation temperature (° C.) | Char yield at 700° C. in N$_2$ (%) | Tg (° C.) |
| --- | --- | --- | --- | --- |
| Control Ex. 1 | 389 | 467 | 12 | 136 |
| Control Ex. 1 | 370 | 376 | 21 | 150 |
| Example 1 | 397 | 499 | 26 | 161 |
| Example 2 | 397 | 501 | 26 | 161 |
| Example 3 | 423 | 523 | 30 | 174 |
| Example 4 | 427 | 528 | 31 | 176 |

TABLE 3

The flame-retardant properties (UL-94V test)

| Specimens | Content of P or Br | Burning time (sec) | Drip | Fume | Classification |
| --- | --- | --- | --- | --- | --- |
| Control Ex. 1 | 0 | 93 | yes | no | V-2 |
| Control Ex. 2 | Br, 17.26% | <1 | yes | yes | V-0 |
| Example 1 | P, 2.12% | 0 | no | no | V-0 |
| Example 2 | P, 2.01% | 0 | no | no | V-0 |
| Example 3 | P, 1.85% | 0 | no | no | V-0 |
| Example 4 | P, 1.80% | 0 | no | no | V-0 |

Tables 1, 2, and 3 show that the cured epoxy resins of the present invention have good mechanical and thermal properties, and have excellent flame-retardant properties, especially no fume and dripping occur in the combustion test, and thus is very suitable for the printed circuit board applications.

IV. Using Phosphorus-Containing Bisphenol A as a Curing Agent for Epoxy Resin

Example 6

Various amounts of DOPO-BQ were added to phenol formaldehyde novolac (PN) as a curing agent for cresol formaldehyde novolac epoxy resin (CNE) to determine the flame-retardant effect of phosphorus. The curing agents consisting of DOPO-BQ/PN in various weight ratios (0/100, 25/75, 50/50, 75/25, and 100/0) were prepared. Triphenyl phosphine ($Ph_3P$) powder was used as a curing accelerator. The CNE was mixed with the above curing agents and 0.2 wt % $Ph_3P$ in a mill at 25° C. to give thermosettable epoxy resin powders, wherein the equivalent ratio of epoxide group to hydroxyl group is 1:1. The resin powders were cured in a mould at 150° C. and 50 kg/cm2 for a period of one hour and then at 200° C. for two hours and further postcured at 260° C. for four hours to obtain cured specimens.

For comparison, various weight ratios of tetrabromobisphenol A (TBBA) and PN (25/75, 50/50, 75/25, 100/0) were also used as a curing agent to prepare the cured specimens as above.

The cured specimens were subjected to the thermogravimetric analysis and the UL-94V test. The results are shown in Table 4 and Table 5.

It can be seen from Table 4 that the Tg values of the phosphorus-containing cured epoxy resin specimens of the present invention were about 40° C. higher than those of the conventional bromine-containing cured epoxy resin specimens. Furthermore, the phosphorus-containing cured epoxy resin specimens of the present invention exhibit higher thermal degradation temperatures and higher char yields in comparison with the conventional bromine-containing cured epoxy resin specimens The data in Table 5 show that 1% phosphorus content of the phosphorus-containing cured epoxy resin of the present invention can produce substantially the same flame-retardant effect as 7~10% bromine content of the conventional bromine-containing cured epoxy resin. In addition, the phosphorus-containing cured epoxy resin specimens of the present invention generate much less fumes in the combustion test.

The results shown in Tables 5 and 6 indicate that the phosphorus-containing cured epoxy resin of the present invention is very suitable for semiconductor encapsulation applications.

TABLE 4

The thermogravimetric analysis data

| Specimens | Tg (° C.) | Temperature of 5 wt % loss, ° C. | | Temperature of 10 wt % loss, ° C. | | Char yield at 700° C., % | |
|---|---|---|---|---|---|---|---|
| | | In air | In N2 | In air | In N2 | In air | In N2 |
| DOPO-BQ/PN | | | | | | | |
| 0/100 | 182 | 397 | 397 | 419 | 419 | 26 | 32 |
| 25/75 | 183 | 401 | 405 | 420 | 421 | 32 | 40 |
| 50/50 | 184 | 408 | 415 | 417 | 425 | 32 | 41 |
| 75/25 | 185 | 411 | 411 | 425 | 427 | 34 | 44 |

TABLE 4-continued

The thermogravimetric analysis data

| Specimens | Tg (° C.) | Temperature of 5 wt % loss, ° C. | | Temperature of 10 wt % loss, ° C. | | Char yield at 700° C., % | |
|---|---|---|---|---|---|---|---|
| | | In air | In N2 | In air | In N2 | In air | In N2 |
| TBBA/PN | | | | | | | |
| 100/0 | 185 | 411 | 413 | 427 | 431 | 38 | 49 |
| 25/75 | 146 | 284 | 403 | 339 | 418 | 26 | 36 |
| 50/50 | 135 | 387 | 396 | 391 | 399 | 26 | 38 |
| 75/25 | 126 | 371 | 390 | 385 | 395 | 28 | 38 |
| 100/0 | 113 | 389 | 409 | 389 | 411 | 28 | 39 |

TABLE 5

The flame-retardant properties (UL-94V test)

| Specimens DOPO-BQ/PN | P % | Burning Time (sec) | Fume[a] | Classification |
|---|---|---|---|---|
| 0/100 | 0 | 85.6 | – | V-2 |
| 25/75 | 1.1 | 8.3 | – – | V-0 |
| 50/50 | 2. | <1 | – – | V-0 |
| 75/25 | 3.1 | 0 | – – | V-0 |
| 100/0 | 4.4 | 0 | – – | V-0 |

TABLE 6

The flame-retardant properties (UL-94V test)

| Specimens DOPO-BQ/PN | P % | Burning time (sec) | Fume[a] | Classification |
|---|---|---|---|---|
| 0/100 | 0 | 85.6 | – | V-2 |
| 25/75 | 1.1 | 8.3 | – – | V-0 |
| 50/50 | 2.0 | <1 | – – | V-0 |
| 75/25 | 3.1 | 0 | – – | V-0 |
| 100/0 | 4.4 | 0 | – – | V-0 |
| TBBA/PN | Br % | | | |
| 25/75 | 5.8 | 16 | ++ | V-1 |
| 50/50 | 12.9 | <1 | ++ | V-0 |
| 75/25 | 22.1 | 0 | + | V-0 |
| 100/0 | 34.4 | 0 | – | V-0 |

[a]++: heavy; +: slightly; –: scarcely; – –: no fume.

What is claimed is:

1. A method for improving flame-retardant properties and flexural strength of an epoxy resin comprising reacting said epoxy resin with a phosphorus-containing dihydric phenol or naphthol having the following formula (III):

(III)

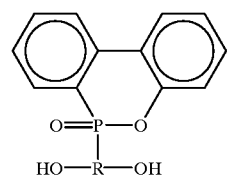

wherein

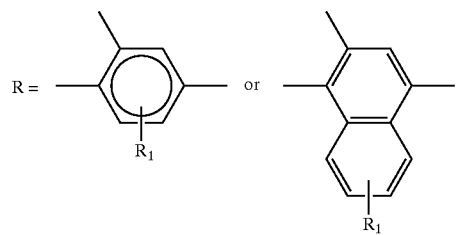

wherein $R_1$ is hydrogen or $C_{1-4}$ hydrocarbon group, in which an epoxide group of said epoxy resin is reacted with a hydroxyl group of said phosphorus-containing dihydric phenol or naphthol so that an open ring reaction of said epoxide group is carried out.

2. The method according to claim 1, wherein

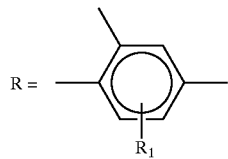

wherein $R_1$ is hydrogen or —$CH_3$.

3. The method according to claim 1, wherein said epoxy resin has the following formula (II):

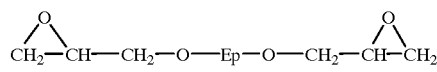

(II)

wherein $E_p$ is

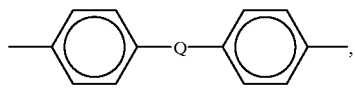

wherein

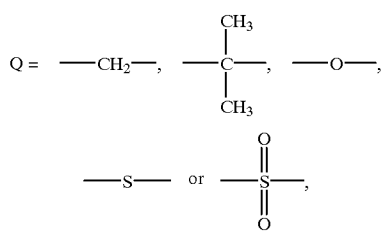

or a phenol-aldehyde novolac epoxy resin backbone having the following formula:

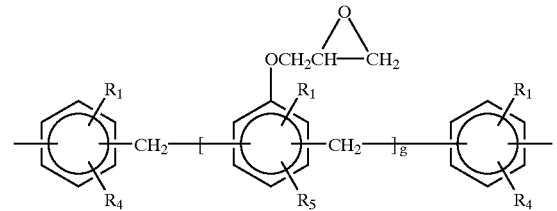

wherein $R_1$ is hydrogen and $R_4$ is —$CH_3$.

4. The method according to claim 3, wherein $E_p$ is

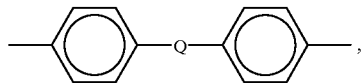

wherein Q is —$C(CH_3)_2$—.

5. The method according to claim 3, wherein $E_p$ is a phenol-aldehyde novolac epoxy resin backbone.

* * * * *